US012266120B2

(12) United States Patent
Piper

(10) Patent No.: US 12,266,120 B2
(45) Date of Patent: Apr. 1, 2025

(54) SYSTEM AND METHOD FOR PREDICTIVE FUSION

(71) Applicant: MIM SOFTWARE INC., Cleveland, OH (US)

(72) Inventor: Jonathan William Piper, Orange, OH (US)

(73) Assignee: MIM SOFTWARE INC., Cleveland, OH (US)

( * ) Notice: Subject to any disclaimer, the term of this patent is extended or adjusted under 35 U.S.C. 154(b) by 0 days.

(21) Appl. No.: 18/109,376

(22) Filed: Feb. 14, 2023

(65) Prior Publication Data
US 2024/0062396 A1   Feb. 22, 2024

Related U.S. Application Data

(63) Continuation of application No. 16/848,022, filed on Apr. 14, 2020, now Pat. No. 11,580,651, which is a
(Continued)

(51) Int. Cl.
*G06V 10/00* (2022.01)
*A61B 8/00* (2006.01)
(Continued)

(52) U.S. Cl.
CPC ............ *G06T 7/344* (2017.01); *A61B 8/4254* (2013.01); *A61B 8/5261* (2013.01);
(Continued)

(58) Field of Classification Search
CPC .......... G06T 7/344; G06T 7/74; G06T 7/337; G06T 7/0012; G06T 2207/10132;
(Continued)

(56) References Cited

U.S. PATENT DOCUMENTS 6,072,903 A   6/2000   Maki
7,074,185 B2  7/2006   Takeuchi
(Continued)

FOREIGN PATENT DOCUMENTS

EP   1623674      8/2006
JP   2004016268   1/2004
(Continued)

OTHER PUBLICATIONS

Xu et al.; WO2022134698A1 Video processing method and device; Publication Date: Jun. 30, 2022.*

*Primary Examiner* — Amir Alavi
(74) *Attorney, Agent, or Firm* — TUCKER ELLIS LLP; Evan T. Perry

(57) ABSTRACT

An image fusion system provides a predicted alignment between images of different modalities and synchronization of the alignment, once acquired. A spatial tracker detects and tracks a position and orientation of an imaging device within an environment. A predicted pose of an anatomical feature can be determined, based on previously acquired image data, with respect to a desired position and orientation of the imaging device. When the imaging device is moved into the desired position and orientation, a relationship is established between the pose of the anatomical feature in the image data and the pose of the anatomical feature imaged by the imaging device. Based on tracking information provided by the spatial tracker, the relationship is maintained even when the imaging device moves to various positions during a procedure.

17 Claims, 9 Drawing Sheets

Related U.S. Application Data continuation of application No. 15/970,973, filed on May 4, 2018, now Pat. No. 10,621,737.

(60) Provisional application No. 62/501,329, filed on May 4, 2017.

(51) Int. Cl.
    *G06T 7/00*       (2017.01)
    *G06T 7/33*       (2017.01)
    *G06T 7/73*       (2017.01)
    *A61B 5/055*     (2006.01)

(52) U.S. Cl.
    CPC ............ *G06T 7/0012* (2013.01); *G06T 7/337* (2017.01); *G06T 7/74* (2017.01); *A61B 5/055* (2013.01); *A61B 8/523* (2013.01); *A61B 8/58* (2013.01); *G06T 2207/10088* (2013.01); *G06T 2207/10132* (2013.01); *G06T 2207/20221* (2013.01); *G06T 2207/30081* (2013.01); *G06T 2207/30244* (2013.01)

(58) Field of Classification Search
    CPC . G06T 2207/10088; G06T 2207/30081; G06T 2207/30244; A61B 8/4254; A61B 8/523; A61B 8/5261; A61B 8/58; A61B 5/055
    See application file for complete search history.

(56) References Cited

U.S. PATENT DOCUMENTS

| | | | |
|---|---|---|---|
| 7,239,718 B2 | 7/2007 | Park | |
| 7,280,710 B1 * | 10/2007 | Castro-Pareja | G06T 7/35 |
| | | | 382/303 |
| 8,165,347 B2 | 4/2012 | Heinzmann | |
| 8,226,560 B2 | 7/2012 | Arai | |
| 8,241,215 B2 | 8/2012 | Takeuchi | |
| 8,345,927 B2 | 1/2013 | Ishikawa | |
| 8,401,251 B2 | 3/2013 | Sasahara | |
| 8,452,080 B2 | 5/2013 | Engedal | |
| 8,711,206 B2 | 4/2014 | Newcombe | |
| 8,781,162 B2 | 7/2014 | Zhu | |
| 9,098,766 B2 | 8/2015 | Dariush | |
| 9,259,204 B2 | 2/2016 | Tawata | |
| 9,471,981 B2 | 10/2016 | Arai | |
| 10,346,464 B2 | 7/2019 | Ye | |
| 10,366,595 B2 * | 7/2019 | Cao | G06N 5/046 |
| 10,621,737 B2 * | 4/2020 | Piper | A61B 8/4254 |
| 10,674,970 B2 | 6/2020 | Averbuch | A61B 6/487 |
| 10,691,950 B2 * | 6/2020 | Cao | G06V 40/103 |
| 11,210,570 B2 * | 12/2021 | Shen | H04N 5/33 |
| 11,562,502 B2 * | 1/2023 | Wallack | H04N 13/246 |
| 11,769,016 B2 * | 9/2023 | Theobald | G06F 18/24 |
| | | | 704/9 |
| 2004/0019270 A1 | 1/2004 | Takeuchi | |
| 2012/0310092 A1 | 12/2012 | Yawata | |
| 2013/0338477 A1 | 12/2013 | Glossop | |
| 2014/0193053 A1 | 7/2014 | Kadoury | |
| 2016/0191903 A1 | 6/2016 | Zhang | |
| 2017/0300116 A1 * | 10/2017 | Lyons | G06F 3/016 |
| 2021/0074008 A1 * | 3/2021 | Piper | G06T 7/337 |
| 2021/0289227 A1 * | 9/2021 | Zhu | G06V 10/764 |
| 2021/0342656 A1 * | 11/2021 | Mittal | G06F 18/2113 |
| 2024/0062396 A1 * | 2/2024 | Piper | A61B 8/5261 |

FOREIGN PATENT DOCUMENTS

| | | |
|---|---|---|
| JP | 2009273597 | 11/2009 |
| JP | 2012245230 | 12/2012 |
| JP | 2016202351 | 12/2016 |
| WO | 2004098414 | 11/2004 |

* cited by examiner

SYSTEM AND METHOD FOR PREDICTIVE FUSION

CROSS-REFERENCE TO RELATED APPLICATIONS

This application is a continuation of U.S. application Ser. No. 16/848,022, filed on Apr. 14, 2020, which is a continuation of U.S. application Ser. No. 15/970,973, filed on May 4, 2018. application Ser. No. 15/970,973 claims priority to U.S. Provisional Application Ser. No. 62/501,329, filed on May 4, 2017. The entireties of the aforementioned applications are herein incorporated by reference.

BACKGROUND OF THE INVENTION

1. Field of the Invention

This application relates generally to image registration and fusion and, more particularly, to systems and methods for facilitating image registration and fusion via spatial tracking of an imaging device.

2. Description of Related Art

Image fusion generally relates to combining information from different images into a single, composite image. In medical imaging, for instance, fusion can involve registering and combining different images, in some manner, to generate a composite image. The composite image can provide improved image quality or enhance usability of the images for diagnosis, treatment planning and assessment, tracking disease progression, etc. In medical imaging, the two or more images fused can be of the same imaging modality or different imaging modalities. Multiple images of the same modality may be fused to ascertain disease progression or treatment efficacy. Images of different modalities can be combined to leverage benefits of the differing modalities or for convenience.

For instance, magnetic resonance imaging (MRI) provides good soft tissue contrast. Thus, Mill provides relatively easy differentiation of lesions or other abnormalities from healthy tissue. Accordingly, Mill performs well for detection and planning. With image-guided procedures, Mill can be inconvenient due to cost and non-portability of the imaging machine. For example, taking a biopsy of a prostate is often guided by ultrasound, which is portable and provides high spatial resolution. Compared to MRI, however, ultrasound provides less tissue discrimination. Thus, an MRI-ultrasound fusion can combine information from the respective modalities to improve execution of the image-guided procedure.

BRIEF SUMMARY OF THE INVENTION

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the sole purpose of the summary is to present some concepts related to some exemplary non-limiting embodiments in a simplified form as a prelude to the more detailed description of the various embodiments that follow.

In various, non-limiting embodiments, an image fusion system provides a predicted alignment between images of different modalities and synchronization of the alignment, once acquired. A spatial tracker detects and tracks a position and orientation of an imaging device within an environment. The imaging device, for instance, is a suitable device for intra-procedural imaging. Based on image data of a different modality to the imaging device, a predicted pose of an anatomical feature can be determined with respect to a desired position and orientation of the imaging device. When the imaging device is moved into the desired position and orientation, a relationship is established between the pose of the anatomical feature in the image data and the pose of the anatomical feature imaged by the imaging device. Based on tracking information provided by the spatial tracker, the relationship is maintained even when the imaging device moves to various positions during a procedure These and other embodiments are described in more detail below.

BRIEF DESCRIPTION OF THE DRAWING

Various non-limiting embodiments are further described with reference the accompanying drawings in which.

DETAILED DESCRIPTION OF THE INVENTION

General Overview

Figure 1:
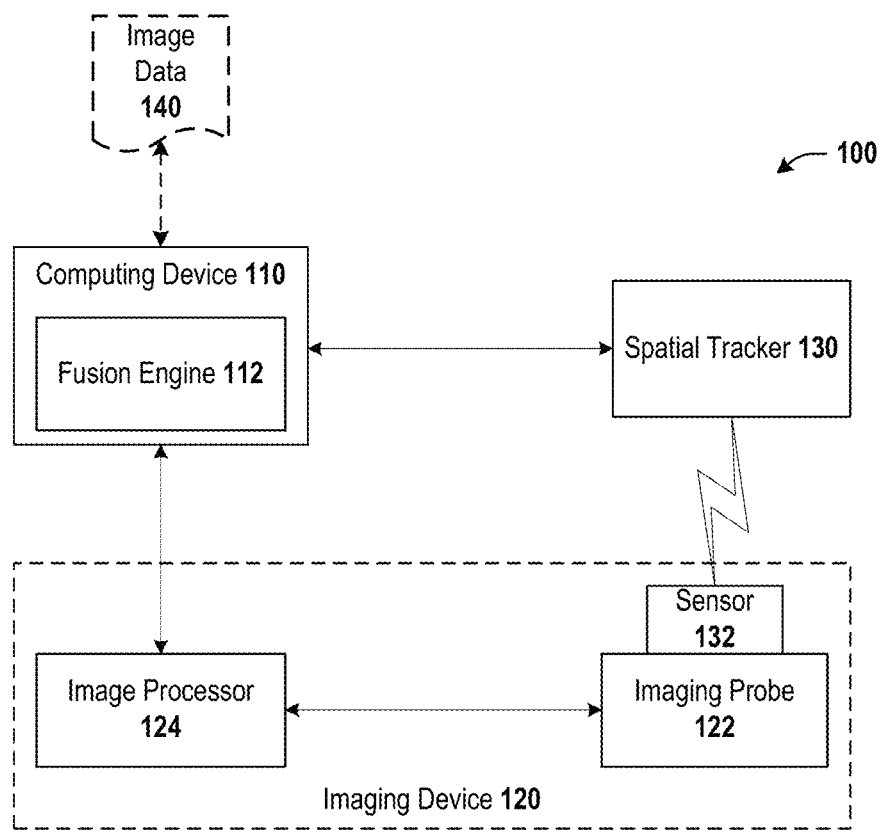
FIG. 1 is a block diagram of an exemplary, non-limiting embodiment for an image fusion system according to one or more aspects.

As discussed in the background, medical image fusion can leverage strengths of different imaging modalities and generate combined information having a wide array of applications. For example, a fusion of Mill and ultrasound images of a prostate can provide effective intra-procedural images with accurate identification of anatomical features. Due to many factors, however, the respective orientations of the prostate in Mill images and intra-procedural ultrasound images can vary significantly. These significant differences result in computationally difficult and imperfect registrations between the two modalities.

In various, non-limiting embodiments, a system and associated methods are provided for image fusion. Based on a live image provided by a spatially tracked imaging device, it can be determined whether the imaging device aligns to a desired position and orientation with respect to an anatomical feature. In particular, the desired position and orientation can be designated based on feature information associated with previously acquired image data, which may be a different modality than the live image. The feature information specifies a position and orientation of the anatomical feature in the previously acquired image data. This image data and feature information can be transformed so as to indicate a pose of the feature as viewed from the perspective of the imaging device in the desired position and orientation.

Once aligned to the desired position and orientation, the relationship between the live image and the previously acquired image data can be established. When locked, tracking information from a spatial tracker can inform processing of the previously acquired image data. Specifically, the image data and/or feature information is transformed in response to movement of the imaging device to maintain alignment. For instance, a spatial transformation between a current spatial position and a reference spatial position (i.e., the desired position and orientation) can be determined based, at least in part, on the tracking information. A corresponding transformation, based on the spatial transformation, can subsequently be applied to the previously acquired image and/or feature information.

In one embodiment, a system is provided that includes a processor coupled to memory storing computer-executable instructions. When executed by the processor, the instructions configure the processor to: obtain feature information indicative of a pose of a feature in a first image of a first modality; obtain tracking information, with at least three degrees of freedom, from a spatial tracker configured to identify a position and orientation of a handheld imaging device producing images of a second modality; and determine when a pose of the imaging device matches a predetermined pose suitable to produce a second image of the feature having a pose that matches a reference pose of the feature based on at least one of the feature information or the tracking information. According to one example, the feature information specifies an orientation of the feature in the first image relative to a given orientation of the imaging device. For instance, the feature information can include a contour of the feature in the first image.

The processor can be further configured to update responsive to movement of the imaging device, an indication of the pose of the feature in the second image produced by the imaging device based on at least one of the tracking information or the feature information. The processor can be further configured to obtain a relationship between the pose of the imaging device in space and a pose of an imaging plane of the imaging device and update the indication of the pose of the feature in the second image based on the relationship. In addition, a spatial relationship between a current pose of the imaging device and a reference pose of the imaging device is also determined, for example, based on the tracking information. The reference pose of the imaging device can correspond to the predetermined pose mentioned above, for instance. To update the indication of the pose of the feature, the processor can be configured to reslice the first image along a virtual imaging plane. The processor can be configured to determine the virtual imaging plane based on the tracking information. In addition, the processor can be configured to interpolate image data of the first image corresponding to the virtual imaging plane. In yet another example, the processor can be configured to identify a transform between the first image and the second image and to apply the transform to the feature information.

Still further, the processor can be configured to display a live image acquired from the imaging device. The processor can also be configured to display an overlay on the live image based on the feature information. In addition, the processor can be configured to update the overlay based on the indication of the pose of the feature in the second image as acquired by the imaging device.

According to another aspect, a method is described. The method includes acquiring a live image of a first modality from an imaging device. In addition, the method can include acquiring tracking information from a spatial tracker that indicates a position and orientation of the imaging device. Further, the method can also include determining when the imaging device is in a desired pose relative to a feature in the live image thereby establishing a relationship between a pose of the imaging device to a pose of the feature in a second image of a second modality, wherein determining the imaging device is in the desired pose is based on at least one the tracking information or feature information indicative of the pose of the feature in the second image.

According to an example, the method can include updating an indication of the feature in the live image, responsive to movement of the imaging device, based on at least one of the tracking information or the established relationship. The indication of the feature can be initially generated based on feature information indicating the pose of the feature in the second image with respect to the desired pose of the imaging device relative to the feature. The feature information can be a contour, for instance. Updating the indication of the feature can include reslicing the second image along a virtual imaging plane, wherein the virtual imaging plane is determined based on the tracking information. Reslicing, in turn, can include interpolating image data of the second image corresponding to the virtual imaging plane. In another example, updating the indication of the feature can include determining a transform between the desired pose of the imaging device and the position and orientation of the imaging device provided by the tracking information, and applying the transform to the indication of the feature.

In yet another embodiment, a computer-readable storage medium is described. The computer-readable storage medium stores computer-executable instructions that, when executed by a processor, configure the processor to: obtain feature information indicative of a feature in a first image of a first modality and a pose of the feature in the first image with respect to a desired pose of an imaging device configured to produce images of a second modality; obtain tracking information from a spatial tracker configured to track a position and orientation of the imaging device in space with at least three degrees of freedom; and determine when the imaging device is aligned with the desired pose based on at least one of a live image produced by the imaging device, the feature information, or the tracking information.

In an example, the computer-executable instructions stored on the computer-readable storage medium further configure the processor to update an indication of the feature in the live image based on at least one of the tracking information or the feature information. For instance, the medium can include instructions that configure the processor to reslice the first image along a virtual imaging plane determined based on the tracking information and interpolate the feature information along the virtual imaging plane to generate an updated indication of the pose of the feature in the live image. In another example, the computer-executable instructions stored on the computer-readable storage medium further configure the processor to determine a transform between the desired pose and the position and orientation of the imaging device provided by the tracking information; and to apply the transform to the feature information to update the indication of the pose of the feature in the live image. In addition, the medium further stores instructions that configure the processor to display an initial indication of the pose of the feature in the live image, wherein the initial indication is generated based on the feature information and provides a guide to align the imaging device with the desired pose.

An overview of some embodiments of predictive fusion has been presented above. As a roadmap for what follows next, predictive image fusion is described in more detail. Afterwards, an exemplary computing device and computing environment, in which such embodiments and/or feature described above can be implemented, are described. The above noted features and embodiments will be described with reference to the drawings, wherein like reference numerals are used to refer to like elements throughout.

Predictive Image Registration and Fusion

As mentioned above, in various embodiments, a fusion of images of different modalities can be determined and alignment between the images can be locked even with an imaging device providing live images and capable of free-form movement in space.

FIG. 1 shows a block diagram illustrating an exemplary, non-limiting embodiment for an image fusion system 100. As shown, image fusion system 100 can include a computing device 110, an imaging device 120, and a spatial tracker 130. The computing device can include a processor and various computer-readable storage media (e.g., volatile and non-volatile). The computer-readable storage media can store computer-executable instructions implementing at least a portion of functional modules, such as fusion engine 112, described herein. When the computer-executable instructions are executed by the processor, the image fusion system 100 is thus configured to perform the operations described herein.

Computing device 110 can further include various hardware devices (not shown) to implement portions of fusion engine 112. For instance, computing device 110 can include a graphics device having a graphics processing unit (GPU), dedicated memory, and/or hardware interfaces to couple the graphics device to a display. Moreover, computing device 110 can include physical hardware ports and/or wireless interfaces (e.g., Bluetooth, wireless USB, etc.) to couple computing device 110 to various devices of image fusion system 100, such as, but not limited to, imaging device 120 and spatial tracker 130.

Imaging device 120, as shown, can include an imaging probe 122 and an image processor 124. In an aspect, imaging device 120 can be a relatively inexpensive and portable device suitable for intra-procedural imaging, such as an ultrasound imaging device. Nonetheless, it is to be appreciated that features and aspects described and claimed herein are not limited to ultrasound applications and can be readily adapted for use with other imaging modalities.

In the ultrasound example, imaging probe 122 can include one or more transducer arrays configures to emit ultrasonic pulses and receive echoes. The echoes can be converted to electrical signals and provided to image processor 124 to generate an ultrasound image. While the image processor 124 is shown separate from computing device 110, it is to be appreciated that processing of echo signals can be performed by computer device 110. For example, a separate software application or a module of fusion engine 112 can be configured to process signals from imaging probe 122. Moreover, while imaging device 120 is shown as including both the imaging probe 122 and the image processor 124, the term "imaging device" as utilized herein can refer to all components that collectively interoperate to generate an image or, depending on context, can refer to the portion housing the transducer arrays (i.e. the probe). For instance, it is to be appreciated that, when described in connection with spatial tracking, the term "imaging device" means the portion of an overall imaging apparatus that is capable of manipulation in order to direct or target what is ultimately imaged.

In an aspect, a sensor 132 can be coupled to or integrated with imaging probe 122. Sensor 132 cooperates with spatial tracker 130 to generate tracking information indicative of a position and orientation of the imaging probe 122 in space. According to an example, spatial tracker 130 can be an electromagnetic (EM) tracking system comprising an EM source that generates a EM field, which establishes a three-dimensional frame of reference. Pursuant to this example, sensor 132 can include induction coils or other devices, which are orthogonally aligned, and generate signals indicative of strength of the received EM field. The signals enable determination of a position and orientation of the sensor 132 in the three-dimensional frame of reference established by the EM source. The signals can be transmitted to the computing device 110, via a wired or wireless connection, for processing and position determination. In the EM tracking system, for example, the signals are typically communicated by sensor 132. Alternatively, however, the signals can be received by spatial tracker 130 and, subsequently, forwarded to computing device 110, with pre-processing or in a raw format. Further, while the above examples contemplate an EM-based positioning system, it is to be appreciated that other trackers can be utilized. For example, spatial tracker 130 can be an accelerometer/gyroscopic-based tracker, an infrared tracker, an optical tracker, an acoustic tracker, a laser tracker, an RF-based tracker, or substantially any other type of spatial tracking and positioning system capable of identifying a position and orientation of a sensor within a frame of reference, such as but not limited to, mechanical spatial tracking (e.g. a probe stepper or gantry).

In a further aspect, sensor 132 is coupled to or integrated with imaging probe 122 so as to establish a known relationship between the location of sensor 132 relative to imaging planes of probe 122. Accordingly, based on this relationship, the position and orientation of the imaging planes (and generated images) within the spatial frame of reference provided by spatial tracker 130 are also known. The relationship between the location of sensor 132 and the imaging planes can be determined by measuring the relationship (i.e., explicitly designed by a probe manufacturer) or by calibration. By way of illustration, one technique to calibrate or establish the known relationship between the location of sensor 132 in the spatial frame of reference and the imaging planes involves imaging a control object. For example, an object (e.g., an intersection point of several threads) can be imaged in a bucket of water from a variety of positions and/or orientations. A spatial transform is then determined, which solves the relationship between pixels in the images identified as the object and the sensor's position in the spatial frame of reference. For instance, the spatial transform can be the solution to a system of linear equations including several unknown variables (translations and rotations in space) and the multiple images acquired of the object. The system of linear equations can be overdetermined such that the number of images acquired is greater than the number of unknowns. It is to be appreciated that the above technique is merely illustrative and other calibration techniques can be utilized.

Fusion engine 112 utilizes this relationship to facilitate fusion between images produced by imaging device 120 and image data 140, which can include previously acquired image data of a different modality, for example. To illustrate, consider an image-guided biopsy of the prostate. Image data 140 can include imaging of the prostate in a different modality from that produced by the imaging device 120. The modality of image data 140 may provide better tissue discrimination capabilities so that the prostate can be readily identified and healthy tissue of the prostate can be differentiated from abnormal tissue.

The location or pose of the prostate in the previously acquired image as well as the location or pose of abnormal tissue can be specified by feature information. In an example, feature information can include a contour of the prostate and a separate contour for the abnormal tissue. In general, however, the term "feature information" relates to imaging or other data that specifies a pose of a feature or object in medical images. As utilized herein, the term "pose" refers to a position and orientation of an object in a given frame of reference, which can be defined relative to another object. By way of example, the pose of a feature in an image relates to the position and orientation of the feature as shown in the image or within the imaging space or volume. The pose of an imaging device relates to the position and orientation of the imaging device relative to an identified reference (e.g., a feature, a tracking volume, etc.) and can also refer to an orientation of an imaging plane of the imaging device relative to the same identified reference.

With the pose of the feature (e.g., prostate) determined in image data 140, fusion engine 112 can determine a reference position and orientation (or pose) for the imaging device 120 relative to the feature. The reference position can be indicated on a display as, for example, an outline of the feature from a viewpoint of an imaging device in the reference pose. More particularly, an imaging device in the reference pose defines an imaging plane. Image data 140 and/or feature information is resampled along the imaging plane to derive the outline. That is, voxel data or contour data intersecting the imaging plane is utilized to generate the outline, or other indication, of the feature.

Figure 6:
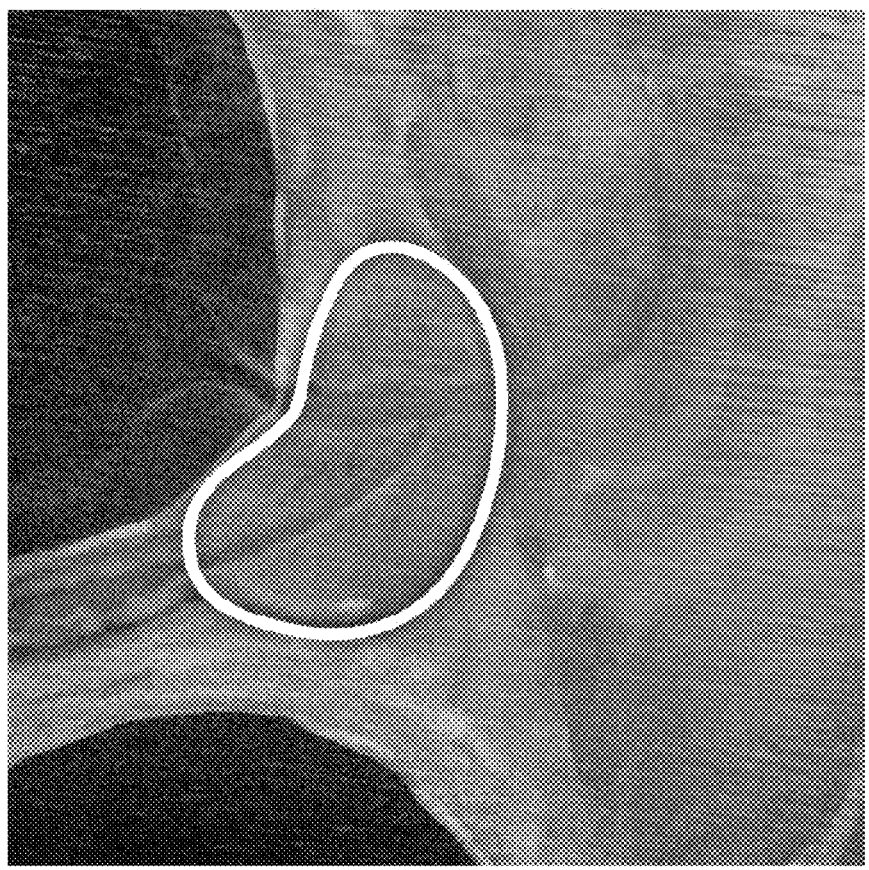
FIG. 6 is an exemplary image having an contour overlaid to indicate a predicted pose of an anatomical feature with respect to a desired position and orientation of an imaging device.
Figure 7:
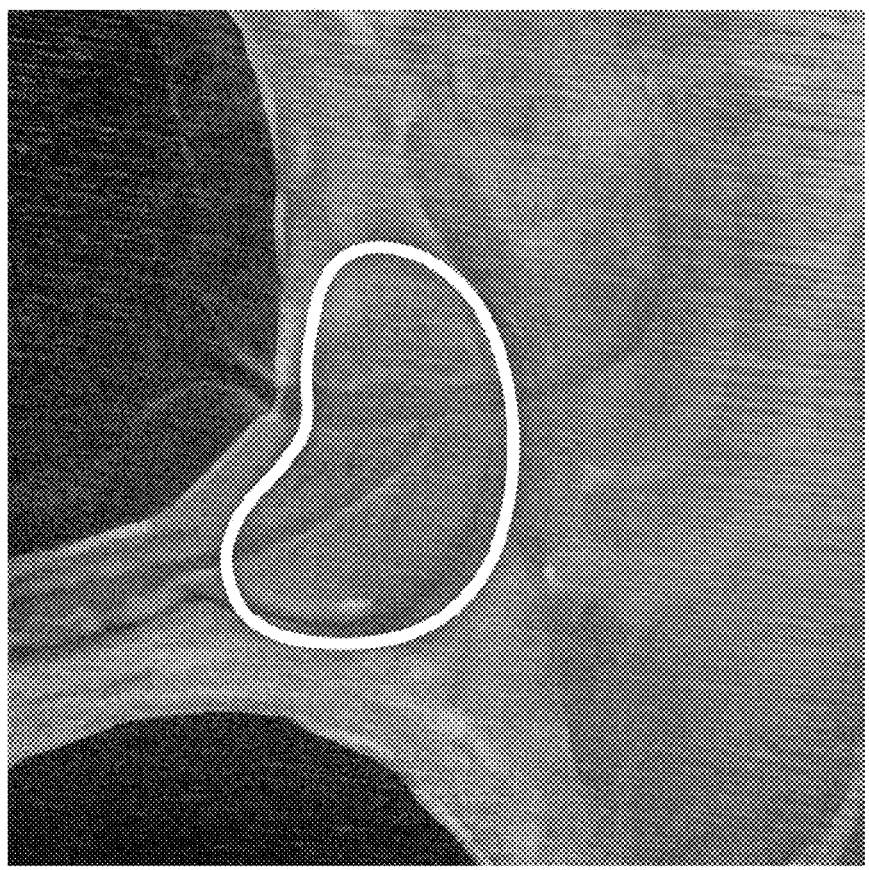
FIG. 7 is an exemplary image captured by the image device subsequent to an operator positioning the imaging device to align the anatomical feature as imaged with the overlaid contour.

Imaging device 120 can generate a live image, which can be displayed by computing device 110. Fusion engine 112 is configured to overlay the outline of the feature on the live image to facilitate alignment. For example, FIG. 6 depicts an exemplary initial image captured by the imaging device 120 and displayed with the outline generated by the fusion engine 112 as described above. An operator manipulates the imaging device 120 until the feature, as shown in the live image, corresponds to the outline. For example, FIG. 7 depicts an exemplary image after the operator manipulates the image device 120 to align the imaged feature to the outline.

Figure 8:
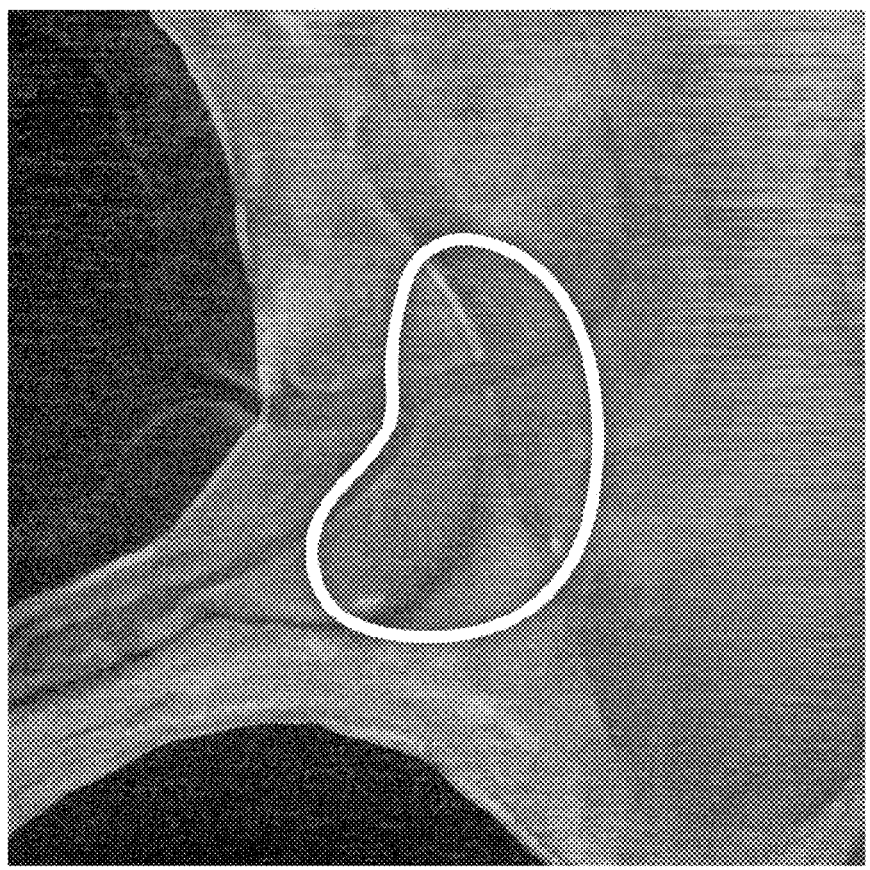
FIG. 8 is an exemplary image captured following movement of the imaging device and after the overlaid contoured is updated responsive to the movement of the image device.

Once a correspondence is achieved, fusion engine 112 can establishes a relationship between the pose of the imaging device 120 in space (i.e. the frame of reference provided by spatial tracker 130) and the pose of the feature in image data 140. Fusion engine 112 employs this relationship to lock in a fusion between the live image and the image data 140. Particularly, the fusion engine 112 maintains alignment between the displayed feature information (e.g., outline) and the pose of the feature in the live image. For example, when the operator moves the imaging device 120, image data 140 is processed and transformed to provide a correspondingly updated outline of the feature displayed over the changing live image (i.e. updates the fusion). For instance, FIG. 8 depicts an exemplary image captured by the imaging device 120 after the operator moves (e.g. tilts) the imaging device 120. In FIG. 8, the outline of the feature is updated in response to the movement of the imaging device to maintain correspondence.

Spatial tracker 130 generates tracking information indicating the pose of the imaging device 120 in space. Fusion engine 112, based on the tracking information, determines a position and orientation of a corresponding imaging plane and reslices the image data 140 along this imaging plane. Feature information (e.g., contours) can also be resliced along the imaging plane to generate the updated outline. Thus, as the operator moves the imaging probe 122 and the live image changes, fusion engine 112 responsively updates feature information derived from the image data 140 to provide a composite image based on the live image and image data 140.

If a patient shifts position, with or without a corresponding movement of the imaging device 120, the relationship between the imaging plane and the feature may change. Accordingly, the relationship (i.e., an initial alignment) may need updated. In another aspect, the computing device 110 may enable the operator to manually adjust the outline or contour to correct the relationship. Alternatively, the fusion engine 112 can relock the relationship. For example, the fusion engine 112 can determine a new reference pose and identify when the features as imaged by the imaging device 120 corresponds to the new reference pose.

Figure 2:
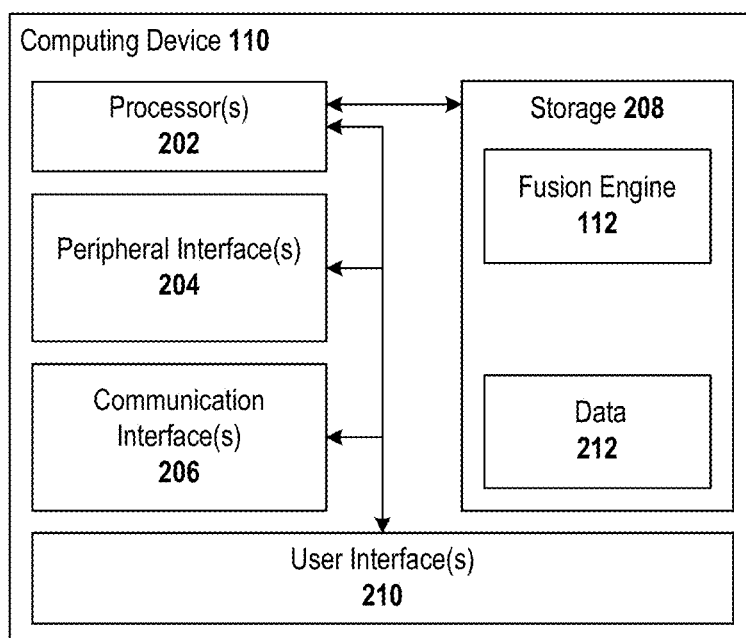
FIG. 2 is a schematic block diagram of an exemplary, non-limiting embodiment for a computing device associated with the image fusion system of FIG. 1.

FIG. 2 illustrates a schematic block diagram of an exemplary, non-limiting embodiment for a computing device 110 associated with image fusion system 100 of FIG. 1. As shown in FIG. 2, computing device 110 includes one or more processor(s) 202 configured to executed computer-executable instructions such as instructions composing fusion engine 112. Such computer-executable instructions can be stored on one or more computer-readable media including non-transitory, computer-readable storage media such as storage 208. For instance, storage 208 can include non-volatile storage to persistently store fusion engine 112 and/or data 212 (e.g., image data, feature information, tracking information, captured image data, configuration information, working data, etc.). Storage 208 can also include volatile storage that stores fusion engine 112 and other data 212 (or portions thereof) during execution by processor 202.

Computing device 110 includes a communication interface 206 to couple computing device 110 to various remote systems (e.g. an image data store, an imaging apparatus, etc.). Communication interface 206 can be a wired or wireless interface including, but not limited, a WiFi interface, an Ethernet interface, a fiber optic interface, a cellular radio interface, a satellite interface, etc. An I/O interface 210 is also provided to couple computing device 210 to various input and output devices such as displays, touch screens, keyboards, mice, touchpads, etc. By way of example, I/O interface 210 can include wired or wireless interfaces such as, but not limited to, a USB interface, a serial interface, a WiFi interface, a short-range RF interface (Bluetooth), an infrared interface, a near-field communication (NFC) interface, etc. Also shown in a peripheral interface 204 to couple computing device 110, wired or wirelessly, to various peripherals utilized by fusion engine 112. For example, peripheral interface 204 can couple computing device 110 to sensor 132 to receive signals, imaging device 120 to receive live images, imaging probe 122 to receive raw signals for processing, and/or spatial tracker 130 to receive tracking information.

Figure 3:
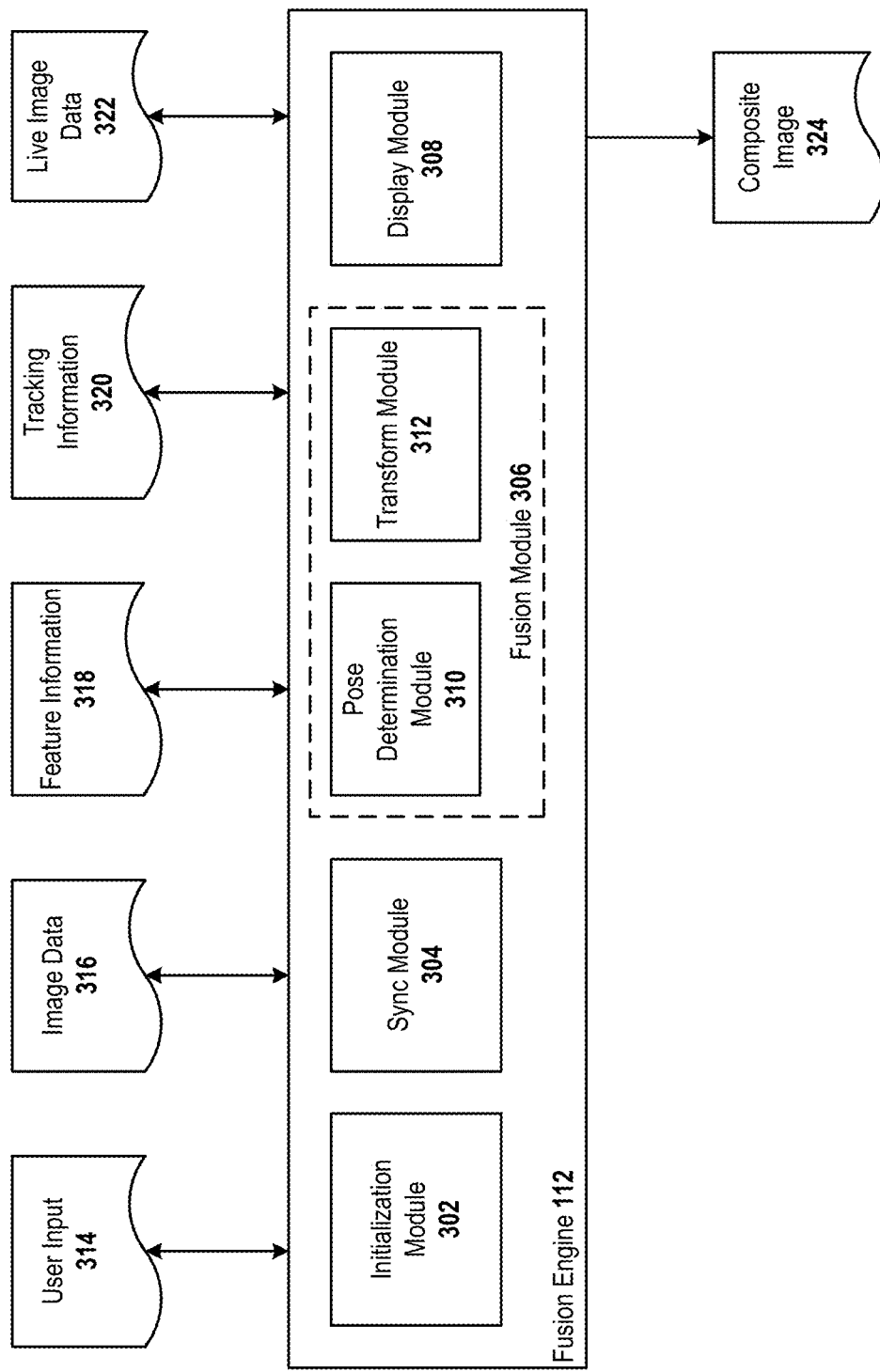
FIG. 3 is a schematic block diagram of an exemplary, non-limiting embodiment for medical image fusion according to one or more aspects.

Turning now to FIG. 3, a block diagram of an exemplary, non-limiting fusion engine 112 is depicted. As shown in FIG. 3, fusion engine 112 can include various functional modules implemented by computer-executable instructions. The modules can include an initialization module 302, a sync module 304, a fusion module 306, and a display module 308.

Initialization module 302 receives user input 314 to configure fusion engine 112 to perform a medical image fusion as disclosed herein. For example, initialization module 302 can load image data 316 from storage, local or remote, based on a selection included in user input 314. Initialization module 302 can also establish a reference pose for an imaging device, which can be a default pose or a pose provided in user input 314. As mentioned above, the reference pose can be a desired pose that can be an initial target pose for the imaging device in order to achieve image fusion in accordance with one or more aspects herein. Based on the reference pose, initialization module 302 can process image data 316 and feature information 318 to generate initial fusion information (e.g., display data or the like) that is combined with live image data 322 by display module 308 to generate composite image 324 displayable on a display.

Sync module 304 determines when the imaging device aligns with the reference pose and locks in a relationship between a pose of imaging device in space and a position and orientation of the feature in image 316 as provided by feature information 318. Sync module 304 can determine alignment based on user input 314. For example, when initial fusion information composited with live image data 322 visually shows alignment between the feature in the live image and the feature from image data 316, an operator can provide input. Alternatively, a registration engine or other image processing modules can evaluate composite image 324, image data 316, feature information 318, and/or live image data 322 to computationally determine alignment.

Once the relationship is established, fusion module 306 maintains the alignment. For instance, fusion module 306 includes a pose determination module 310 that determines a pose of the image device based on tracking information 320 from a spatial tracker. Transform module 312 processes image data 316 and/or feature information 318 to update the fusion information that is combined with live image data 322 to generate composite image 324. As described above, transform module 312 can reslice image data 316 and/or feature information 318 according to a virtual image plane corresponding to an imaging plane of the imaging device in the pose specified by tracking information 320. In another example, a transform can be determined based on tracking information 320 and the determined transform can be directly applied to the fusion information composited with live image data 322.

Figure 4:
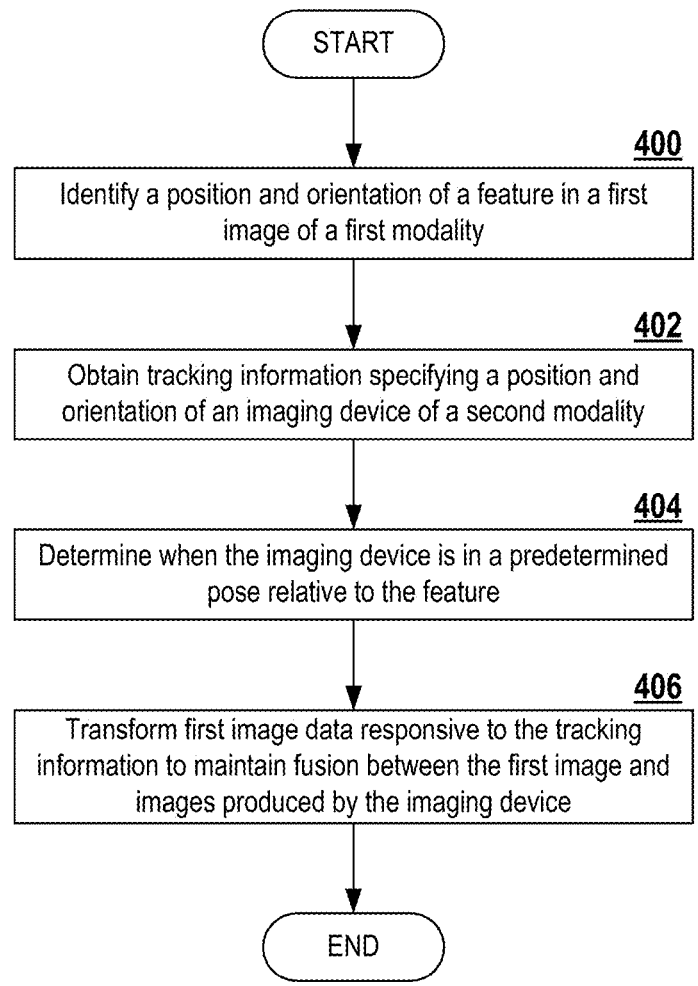
FIG. 4 is a flow diagram of an exemplary, non-limiting method for predicting a fusion between at least two image modalities.

FIG. 4 illustrates a flow diagram of an exemplary, non-limiting method for predicting a fusion between at least two image modalities. The method of FIG. 4 can be performed, for example, by image fusion system 100 and/or fusion engine 112 executed on computing device 110 as described previously. At 400, a position and orientation of a feature in a first image of a first modality is identified. For example, a contour can be defined that indicates the feature in the first image. At 402, tracking information specifying a position and orientation of an imaging device of a second modality is obtained. The tracking information can be acquired by a spatial tracking or other positioning system. At 404, a determination is made when the imaging device is placed in a predetermined pose relative to the feature. The determination can be based on the tracking information, feature information (e.g., contours), image data of the first image, or user input. At 406, first image data and/or associated contours are transformed responsive to the tracking information to maintain alignment between the first image and images produced by the imaging device.

Figure 5:
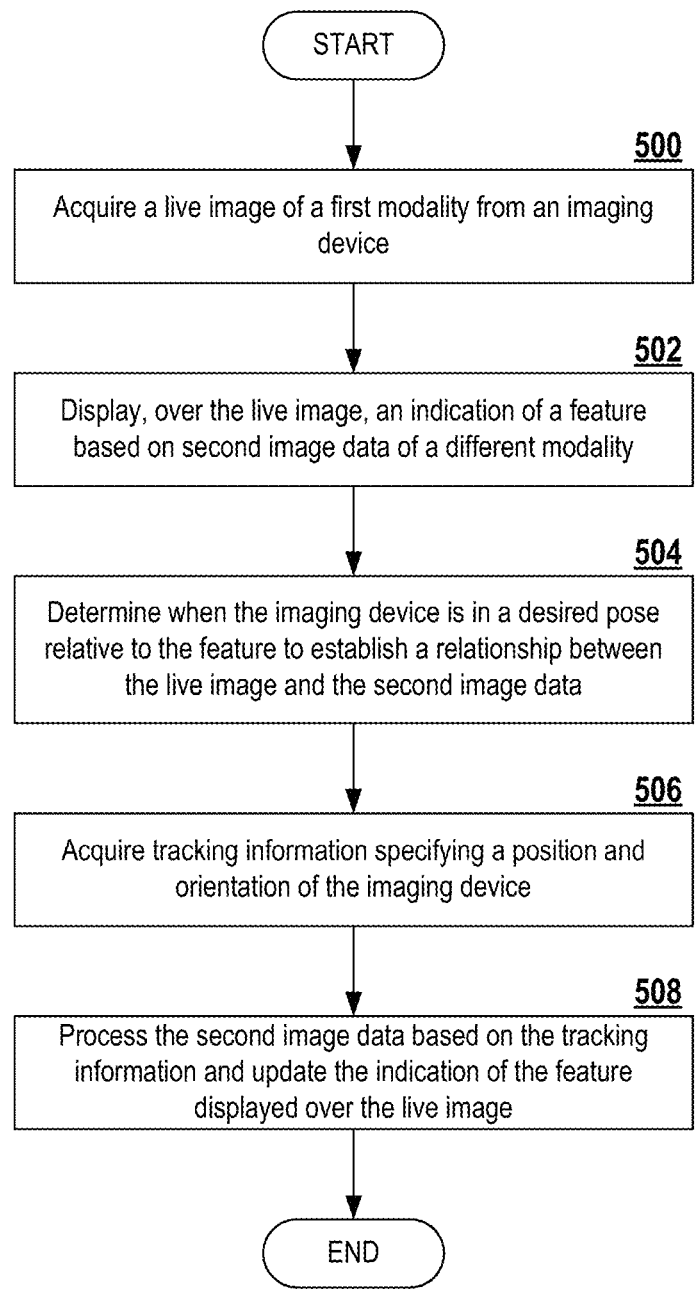
FIG. 5 is a flow diagram of an exemplary, non-limiting method for generating a fusion between a live image and a previously acquired image.

Referring now to FIG. 5, a flow diagram of an exemplary, non-limiting method for generating a fusion between a live image and a previously acquired image is illustrated. The method of FIG. 5 can be performed, for example, by image fusion system 100 and/or fusion engine 112 executed on computing device 110 as described above. At 500, a live image of a first modality is acquired from an imaging device. At 502, an indication of a feature, from a second image of a different modality, is displayed over the live image. At 504, a relationship is established between the live image and the second image when it is determined that the imaging device is in a desired posed relative to the feature. At 506, tracking information is acquired. The tracking information specifies a position and orientation of the imaging device in a reference space. At 508, the second image is processed based on the tracking information to update the indication of the feature and possibly other features, displayed over the live image.

The exemplary embodiments described above are presented in the context of image fusion. It is to be appreciated that these concepts can be extended to other contexts, such as image correlation. For instance, as opposed to combining or compositing (i.e. overlaying) portions of images, the images, or portions thereof, can be displayed side-by-side or in another arrangement for comparison.

Exemplary Computing Device

As mentioned, advantageously, the techniques described herein can be applied to any device where it is desirable to provide predictive fusion and live tracking of images of different modalities. It can be understood, therefore, that handheld, portable and other computing devices and computing objects of all kinds are contemplated for use in connection with the various embodiments of a registration visualization system. Accordingly, the below general purpose computer described below in FIG. 9 is but one example of a computing device.

Embodiments can partly be implemented via an operating system, for use by a developer of services for a device or object, and/or included within application software that operates to perform one or more functional aspects of the various embodiments described herein. Software may be described in the general context of computer-executable instructions, such as program modules, being executed by one or more computers, such as client workstations, servers or other devices. Those skilled in the art will appreciate that computer systems have a variety of configurations and protocols that can be used to communicate data, and thus, no particular configuration or protocol is considered limiting.

Figure 9:
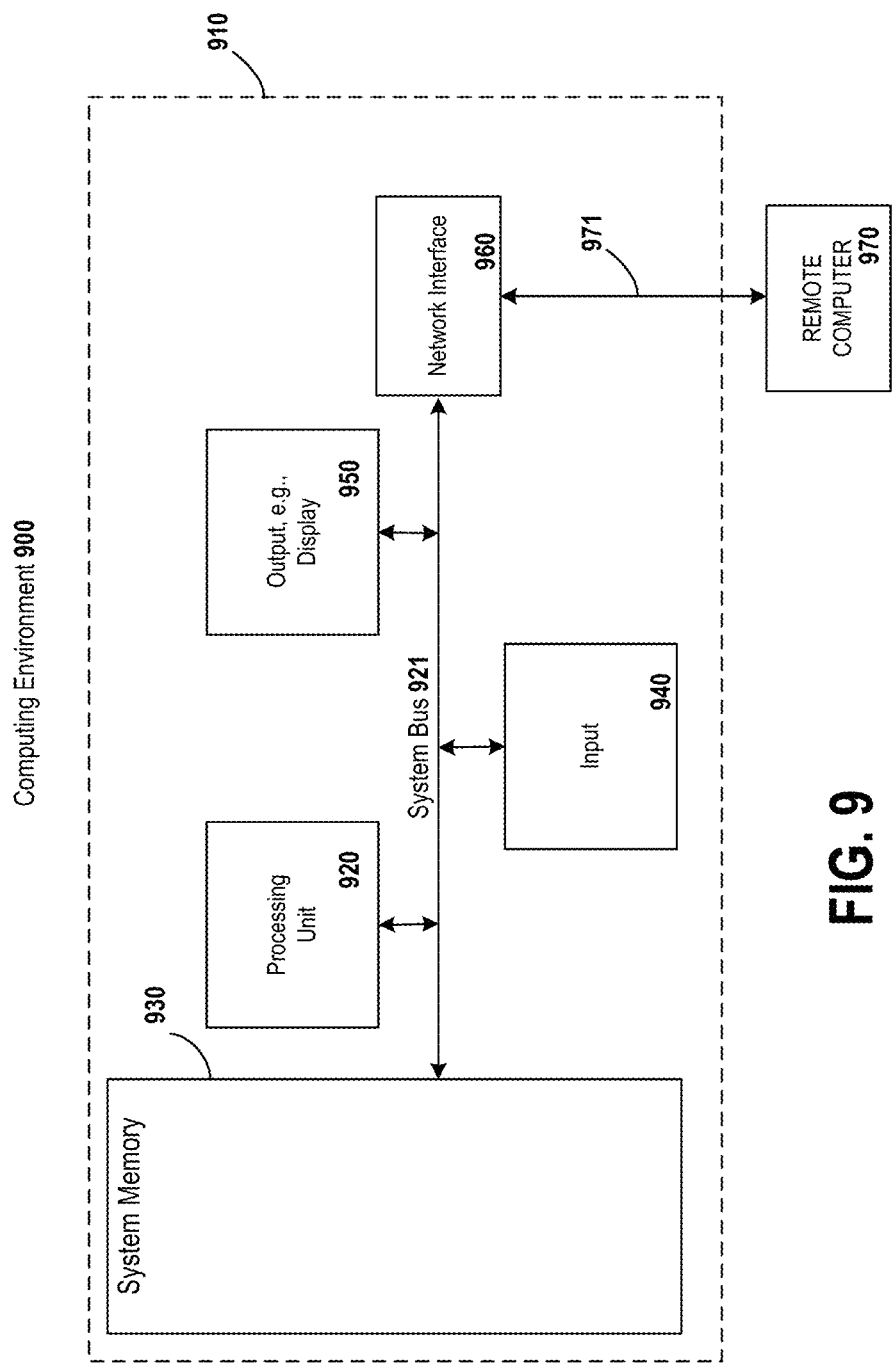
FIG. 9 is a block diagram representing an exemplary, non-limiting computing system or operating environment in which one or more aspects of various embodiments described herein can be implemented.

FIG. 9 thus illustrates an example of a suitable computing system environment 900 in which one or aspects of the embodiments described herein can be implemented, although as made clear above, the computing system environment 900 is only one example of a suitable computing environment and is not intended to suggest any limitation as to scope of use or functionality. In addition, the computing system environment 900 is not intended to be interpreted as having any dependency relating to any one or combination of components illustrated in the exemplary computing system environment 900.

With reference to FIG. 9, an exemplary device for implementing one or more embodiments includes a general purpose computing device in the form of a computer 910. Components of computer 910 may include, but are not limited to, a processing unit 920, a system memory 930, and a system bus 922 that couples various system components including the system memory to the processing unit 920.

Computer 910 typically includes a variety of computer readable media and can be any available media that can be accessed by computer 910. The system memory 930 may include computer storage media in the form of volatile and/or nonvolatile memory such as read only memory (ROM) and/or random access memory (RAM). By way of example, and not limitation, system memory 930 may also include an operating system, application programs, other program modules, and program data. According to a further example, computer 910 can also include a variety of other media (not shown), which can include, without limitation, RAM, ROM, EEPROM, flash memory or other memory technology, compact disk (CD) ROM, digital versatile disk (DVD) or other optical disk storage, or other tangible and/or non-transitory media which can be used to store desired information.

A user can enter commands and information into the computer 910 through input devices 940. A monitor or other type of display device is also connected to the system bus 922 via an interface, such as output interface 950. In addition to a monitor, computers can also include other peripheral output devices such as speakers and a printer, which may be connected through output interface 950.

The computer 910 may include a network interface 960 so as to operate in a networked or distributed environment using logical connections to one or more other remote computers, such as remote computer 970. The remote computer 970 may be a personal computer, a server, a router, a network PC, a peer device or other common network node, or any other remote media consumption or transmission device, and may include any or all of the elements described above relative to the computer 910. The logical connections depicted in FIG. 9 include a network 971, such local area network (LAN) or a wide area network (WAN), but may also include other networks/buses. Such networking environments are commonplace in homes, offices, enterprise-wide computer networks, intranets and the Internet.

As mentioned above, while exemplary embodiments have been described in connection with various computing devices and network architectures, the underlying concepts may be applied to any network system and any computing device or system in which it is desirable to implement an image fusion system.

Also, there are multiple ways to implement the same or similar functionality, e.g., an appropriate API, tool kit, driver code, operating system, control, standalone or downloadable software objects, etc. which enables applications and services to take advantage of the techniques provided herein. Thus, embodiments herein are contemplated from the standpoint of an API (or other software object), as well as from a software or hardware object that implements one or more embodiments as described herein. Thus, various embodiments described herein can have aspects that are wholly in hardware, partly in hardware and partly in software, as well as in software.

As utilized herein, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the term "exemplary" is intended to mean "serving as an illustration or example of something."

Illustrative embodiments have been described, hereinabove. It will be apparent to those skilled in the art that the above devices and methods may incorporate changes and modifications without departing from the general scope of the claimed subject matter. It is intended to include all such modifications and alterations within the scope of the claimed subject matter. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system, comprising:
a processor coupled to memory storing computer-executable instructions that, when executed by the processor, configure the processor to:
obtain feature information indicative of a pose of a feature in a first image of a first modality;
display a live image acquired from an imaging device producing images of a second modality;
display an overlay on the live image based on the feature information, wherein the overlay initially corresponds to a reference viewpoint of the feature; and
update the overlay responsive to movement of the imaging device.

2. The system of claim 1, wherein the processor is further configured to determine when a pose of the imaging device results in a viewpoint of the feature matching the reference viewpoint.

3. The system of claim 1, wherein the processor is further configured to:
obtain tracking information for a spatial tracking configured to identify a position and orientation of the imaging device; and
obtain a relationship between a pose of an imaging plane of the imaging device and the position and orientation of the imaging device indicated by the tracking information.

4. The system of claim 1, wherein the processor is further configured to reslice the first image along a virtual imaging plane corresponding to the imaging plane of the imaging device.

5. The system of claim 1, wherein the feature information is a contour of the feature in the first image.

6. The system of claim 1, wherein the processor is further configured to update the overlay to maintain a pose of the feature from a viewpoint of the imaging device.

7. A method, comprising:
obtaining feature information indicative of a pose of a feature in a first image of a first modality;
displaying a live image acquired from an imaging device producing images of a second modality;
displaying an overlay on the live image based on the feature information, wherein the overlay initially corresponds to a reference viewpoint of the feature; and updating the overlay responsive to movement of the imaging device.

8. The method of claim 7, further comprising determining when a pose of the imaging device results in a viewpoint of the feature matching the reference viewpoint.

9. The method of claim 7, further comprising:
obtaining tracking information for a spatial tracking configured to identify a position and orientation of the imaging device; and
obtaining a relationship between a pose of an imaging plane of the imaging device and the position and orientation of the imaging device indicated by the tracking information.

10. The method of claim 7, further comprising reslicing the first image along a virtual imaging plane corresponding to the imaging plane of the imaging device.

11. The method of claim 7, wherein the feature information is a contour of the feature in the first image.

12. The method of claim 7, further comprising updating the overlay to maintain a pose of the feature from a viewpoint of the imaging device.

13. A non-transitory, computer-readable storage medium having stored thereon computer-executable instructions that configure a processor to:
obtain feature information indicative of a pose of a feature in a first image of a first modality;
display a live image acquired from an imaging device producing images of a second modality;
display an overlay on the live image based on the feature information, wherein the overlay initially corresponds to a reference viewpoint of the feature; and
update the overlay responsive to movement of the imaging device.

14. The non-transitory, computer-readable storage medium of claim 13, further storing instructions that configure the processor to determine when a pose of the imaging device results in a viewpoint of the feature matching the reference viewpoint.

15. The non-transitory, computer-readable storage medium of claim 13, further storing instructions that configure the processor to:
obtain tracking information for a spatial tracking configured to identify a position and orientation of the imaging device; and
obtain a relationship between a pose of an imaging plane of the imaging device and the position and orientation of the imaging device indicated by the tracking information.

16. The non-transitory, computer-readable storage medium of claim 13, further storing instructions that configure the processor to reslice the first image along a virtual imaging plane corresponding to the imaging plane of the imaging device.

17. The non-transitory, computer-readable storage medium of claim 13, further storing instructions that configure the processor to update the overlay to maintain a pose of the feature from a viewpoint of the imaging device.

* * * * *